United States Patent [19]
Karbach et al.

[11] Patent Number: 5,335,546
[45] Date of Patent: Aug. 9, 1994

[54] ULTRASONIC TESTING OF ELONGATED, PRISMSHAPED SECTIONS WITH AT LEAST ONE PLANE OUTER SURFACE EXTENDING ALONG THE LONGITUDINAL AXIS OF THE SECTION

[75] Inventors: Bernhard Karbach, Erftstadt-Friesheim; Reinhard Prause, Augustin; Heinrich Weber, Lindlar-Frielingsd., all of Fed. Rep. of Germany

[73] Assignee: Krautkrämer GmbH & Co., Hürth, Fed. Rep. of Germany

[21] Appl. No.: 761,788
[22] PCT Filed: Mar. 17, 1990
[86] PCT No.: PCT/DE90/00204
§ 371 Date: Sep. 19, 1991
§ 102(e) Date: Sep. 19, 1991
[87] PCT Pub. No.: WO90/11516
PCT Pub. Date: Oct. 4, 1990

[30] Foreign Application Priority Data
Mar. 18, 1989 [DE] Fed. Rep. of Germany ....... 3908967

[51] Int. Cl.$^5$ .............................................. G01N 29/04
[52] U.S. Cl. ......................................... 73/622; 73/644; 73/628; 73/634
[58] Field of Search ................. 73/622, 627, 628, 637, 73/644, 634

[56] References Cited
U.S. PATENT DOCUMENTS

| | | | |
|---|---|---|---|
| 3,969,926 | 7/1976 | Walker et al. | 73/634 |
| 4,084,444 | 4/1978 | Lewis | 73/622 |
| 4,470,307 | 9/1984 | Genter et al. | 73/634 |
| 4,596,953 | 6/1986 | Nagasaka et al. | 73/622 |
| 4,843,884 | 7/1989 | House et al. | 73/622 |

FOREIGN PATENT DOCUMENTS
638890 12/1978 U.S.S.R. ................................ 73/622

Primary Examiner—Hezron E. Williams
Assistant Examiner—Nashmiya Ashraf
Attorney, Agent, or Firm—K. S. Cornaby

[57] ABSTRACT

In a process for ultrasonic testing of elongated, prism-shaped sections (22) with at least one planar outer surface (54) extending along the longitudinal axis (26) of the section, with the objective of detecting material defects or verifying geometric data, the section (22) to be tested is exposed to ultrasonic beams from several ultrasonic probes (28 to 34) installed in a probe carrier (44). The section (22) is moved along its longitudinal axis (26) in relation to the probe carrier (44). The latter is installed in the rotor (20) of a rotary testing machine which rotates around the longitudinal axis (26) of the section (22). The probes (28 to 34) are installed in the probe carrier (44) so that each can be displaced individually, either transversely or, preferably, at right angles to the longitudinal axis (26) if the section (22) and the direction of the probes and/or so that their angular position can be adjusted individually by swivelling them around a swivel axis (58) running parallel to the longitudinal axis (26) of the section (22). The individual probes (28 to 34) are adjusted so that the central beams (46) emitted by each probe (28 to 34) impinge upon the planar outer surface (54) adjacent to one another, thus forming adjacent scanning zones in the volume of the section (22) to be tested. The probes (28 to 34) are triggered individually by an arrangement for determining the angle between the rotor (20) and the section (22); testing is only performed when the angle between the central beam (46 and the planar outer surface (54) lies within a predetermined range.

9 Claims, 2 Drawing Sheets

ULTRASONIC TESTING OF ELONGATED, PRISMSHAPED SECTIONS WITH AT LEAST ONE PLANE OUTER SURFACE EXTENDING ALONG THE LONGITUDINAL AXIS OF THE SECTION

BACKGROUND OF THE INVENTION

The invention relates to a process for ultrasonic testing of elongated, prism-shaped sections with at least one planar outer surface extending along the longitudinal axis of the section, in particular bar sections and tubes, to detect material defects or to verify the geometric data of the sections, and to a device for carrying out this testing process. In the process, the section to be tested is exposed to ultrasonic beams from several ultrasonic probes installed in a probe carrier. The section is moved along its longitudinal axis in relation to the probe carrier.

The testing of elongated, rotationally symmetrical workpieces with rotating ultrasonic probes installed in a rotor is a generally-known process. However, the current state of the art for the testing of elongated, prism-shaped sections employs a simple translation movement between the probe carrier and the section to be tested.

Generally, in this method, only a small portion of the entire cross-sectional area of the section is actually tested; in most cases, a central beam scans the central area of the section, because the probability of finding faults there is relatively high. However, this approach does not provide satisfactory information on freedom from defects across the entire cross-sectional area of the section (and thus in its entire volume). The process according to the current state of the art is also very costly and involved, because a separate set of probes is required for each planar outer surface, and the setup of the testing apparatus must also be completely changed before new sections with different geometry or dimensions can be tested. In the current state of the art, this is achieved by mounting special test assemblies for each section type to be tested. This approach is both cost-intensive and labour-intensive.

Elongated, prism-shaped sections are defined as bodies whose length is significantly longer than the dimensions of their cross-section and whose cross-sectional area is constant over their entire length. In practical applications, the majority of sections to be tested are square or hexagonal and made of solid material; however, the process described at the outset can also be used for testing tubing and rod material with other cross-sections, for example rolled sections, extruded aluminum sections, plastic sections and so on.

On the basis of the process and device of the type described at the outset, the problem of the invention was to achieve a significant increase in the volume percentage covered by the test and a significant reduction in the amount of work required in order to reset the device and test different sections.

SUMMARY OF THE INVENTION

This problem is solved, on the basis of the process of the type described at the outset, as follows: The probe carrier is installed in a rotor which rotates around the longitudinal axis of the section; each ultrasonic probe is installed in the probe carrier so that it can be displaced individually, either transversely or, preferably, at right angles on one hand to the longitudinal axis and on the other hand to the direction of the probe and/or so that its angular position can be adjusted individually by swivelling it around an axis running parallel to the longitudinal axis of the section; the probes are adjusted so that the scanning beams emitted by the probe impinge upon the planar outer surface adjacent to one another (either simultaneously or at different times), thus forming adjacent scanning zones in the volume of the section; the probes are activated individually by an arrangement for determining the angle between the rotor and the section; the probes are only activated when the angle between the probe axis and the planar outer surface lies within a predetermined range, e.g. $90°+/-5°$.

In the device, the problem of the invention is solved as follows: The probe carrier is installed in a rotor which rotates around the longitudinal axis of the section; each probe is installed in the probe carrier so that it can be displaced individually, either transversely or, preferably, at right angles to the longitudinal axis of the section and the direction of the probe and/or so that its angular position can be adjusted individually by swivelling it around an axis running parallel to the longitudinal axis of the section; an arrangement for determining the angle between the rotor and the profile is provided, and said arrangement is connected with a control unit for switching the testing electronics on and off.

This process and the device implementing this process ensure that a sufficient number of ultrasonic probes are allocated to each planar outer surface. In the course of each rotation of the rotor, the points of incidence of the central beams of these probes describe an (invisible) pattern of points or dashes, made up of a number of individual points, on the planar outer surface; these points or short, dash-shaped scanning tracks extend more or less evenly across the planar outer surface, in particular in the edge zones. The central beam of a probe describes a single point when only one scanning impulse is triggered each time the planar outer surface appears (i.e. once per rotation). Usually, however, multiple scanning impulses are triggered each time the planar outer surface appears; these impulses form short, essentially dash-shaped scanning tracks made up of individual points and scanning along a nearly helical line of development. A new pattern of points or dashes is described upon each rotation, and thus each time the planar outer surface appears in front of the probes; the position of each new pattern is at an offset in relation to the previous one, however, because of the longitudinal movement which has taken place during the rotation. Each point or dash made up of individual points corresponds to a test zone in the volume of the section to be tested lying behind the planar outer surface. Since the test can be performed on each planar outer surface limiting the section, it is possible to perform a full test of the entire section in the case of normal sections, for example sections with square or hexagonal cross-sections.

In contrast to testing devices for rotationally symmetrical test specimens, the probes in the process and/or device according to the invention are only triggered when the at least one planar outer surface of the section is within a certain angular range in relation to the probe in question. This is achieved by an arrangement for determining the angle between the rotor and the section, and by the control unit. The latter only triggers the probes when the measured angle between the minimum of one planar outer surface and the probe in question in within the predetermined range.

The process and the device provide two different solutions for the arrangement of the ultrasonic probes. The probes can be either transversely displaceable and/or adjustable in their angular position.

The transversely displaceable probes are usually arranged in a row in the rotor, along the longitudinal axis of the section. They are adjusted in staggered positions, so that the points described by the central beams of all the probes on the at least one planar outer surface are distributed as evenly as possible across the entire outer surface (conceivably at an angle). When so adjusted, the individual probes can be aligned parallel to one another so that they all fall within the predetermined angle range at the same time. The probes can also be arranged on different radial lines and displaced at right angles to the respective radial line so that the individual probes fall within the predetermined angle range at different times, i.e. when the rotor is at different angular positions.

In the case of adjustable-angle probes, the individual probes normally fall within the predetermined angle range at different rotational positions of the rotor. For example, when the predetermined angle range is around 90°, each probe aligned along a radial line is activated when the at least one planar outer surface is essentially at right angles to this radial line. If the probe is swivelled through an angle of 5°, for example, the 90° condition is fulfilled when the rotor is in a different rotational position, roughly 5° away from the first position. Then, however, the central beam of the probe in question no longer impinges on the same point on the planar outer surface, but rather on a point laterally displaced in relation to the first. The individual probes can be adjusted to different angles so that the points or "dashes" of incidence are distributed, preferably evenly, across the width of the outer surface to be scanned, so that here too a test of the entire volume can be realized.

One of the great advantages of the device according to the invention is the fact that it can also be used for testing round material. Essentially, it is thus a universal system.

The use of a rotor for ultrasonic testing of finned tubing is known from DE-OS 25 57 062; in this system, the ultrasonic probes are switched off whenever their scanning beams are in the vicinity of the fins. However, this known process is essentially a modified process for the testing of tubing and round material; the difference is that the test is interrupted when the fins are in the vicinity of the probes. It is thus crucial to the known process that finned tubing consists essentially of tube-like, rotationally symmetrical cross-sections and that the fins can be regarded as a disturbance. Such conditions are not given in the testing of general, elongated, prism-shaped sections. The known process is thus not applicable for the testing of such sections.

It has proven to be very advantageous to make use of the specular reflection of at least one of the ultrasonic probes from the planar outer surface in order to determine the angle between the rotor and the section. In this manner it is possible to determine precisely when the central beam of the probe in question is at right angles to the planar outer surface. This can be achieved without measuring the angular position of the rotor and without a precision feed guide system for the section. The echo signal obtained from the specular reflection of one probe can be used to trigger the other probes; alternatively, it is also possible for the other probes to determine their own positions by registering their own specular reflections and to use the signal thus obtained for triggering. It is possible to derive trigger signals directly from the specular reflection signals; however, it is also possible to time-delay these signals or process them in a computer in order to determine the respective rotational angle of the rotor around the section to be tested at every point in time. This method also allows determination of the length of the section. In a preferred development of the system time gates are used where the reflected echo is assigned to a first (earlier) time gate and the expected defect echo range is assigned to a second (later) time gate; in such a system, the same measurement impulse ("shot") can be used to determine the specular reflection and to perform the actual measurement. The registration of the specular reflection of the echo thus results in no disadvantages for the testing of the section.

In another embodiment, however, it is also possible to use a different arrangement for determining the angle between the rotor and the section, such as that already known from DE-OS 25 57 062, already mentioned above. This consists essentially of an angular encoding of the angle of rotation and a feed guide mechanism to ensure the precise angular position of the section to be tested. A control unit connected to the system only enables the probes when the angle between the individual probe and the planar outer surface is within the predetermined range.

The invention is not restricted to ultrasonic probes whose beams impinge at right angles upon the outer surface being scanned; on the contrary, angled probes can also be used, as can wide-beam probes. The measurement of the geometric data can include, in particular, the verification of the key width of the section being scanned. Other geometric data can also be verified, however; their registration depends upon the availability of reflecting boundary surfaces.

Finally, the process according to the invention can also be developed further so that the connected testing machine can automatically identify the form and dimensions of any section to be tested, with the help of the computer. The perpendicular position of the central testing beam of a probe in relation to a planar outer surface is determined using the reflected signal. Other probes arranged at other angular positions of the rotor can also, in turn, provide additional specular reflection signals. If a sensor is also provided which emits a signal upon each completed rotation of the rotor, e.g. at the 0° position, it becomes possible to derive the shape of the section from the data thus generated. If the time at which the reflected echo is received after emission of the ultrasonic impulse is also registered it also becomes possible to draw a conclusion as to the geometric dimensions of any scanned section. Simple profiles in particular can easily be identified with this approach, e.g. square or hexagonal sections.

The use of a rotor to carry out the testing results in a significant improvement in the volume testing of the test section and also allows significantly better utilization of the installed probes, i.e. it is possible to fire a significantly higher number of individual shots per probe and unit of time than is possible with the process according to the current state of the art.

THE DRAWING

Further features and advantages of the invention are revealed in the remaining claims and the following description of sample embodiments, which should not be understood to be restrictive and which are explained with reference to the attached figures. These figures are as follows:

FIG. 1; A cross-section showing the schematic construction of a rotary testing device for sections with at least one planar outer surface extending along the longitudinal axis of the section.

FIG. 2; A cross-section through line II—II in FIG. 1.

FIG. 3; A schematic representation of an arrangement with transversely displaceable probes seen from the same viewpoint as FIG. 2

FIG. 4; A plan view of the planar outer surface facing the probes, corresponding to a cross-section IV—IV in FIG. 3.

FIG. 5; A representation corresponding to FIG. 3 but showing adjustable-angle probes.

FIG. 6; A plan view of the planar outer surface facing the probes in FIG. 5.

FIG. 7; Example of a typical echo diagram resulting with a perpendicular scanning beam and perpendicular probe position.

DETAILED DESCRIPTION OF THE DRAWING

Figure 1:
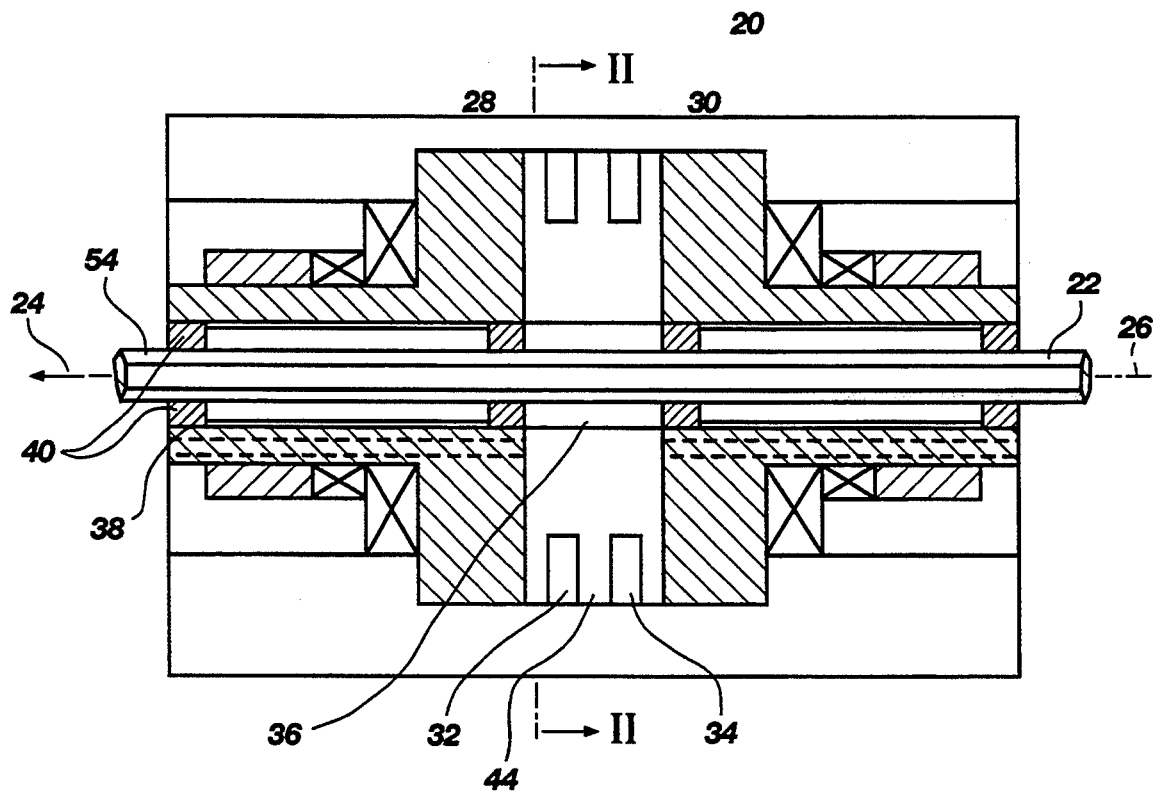
Figure 2:
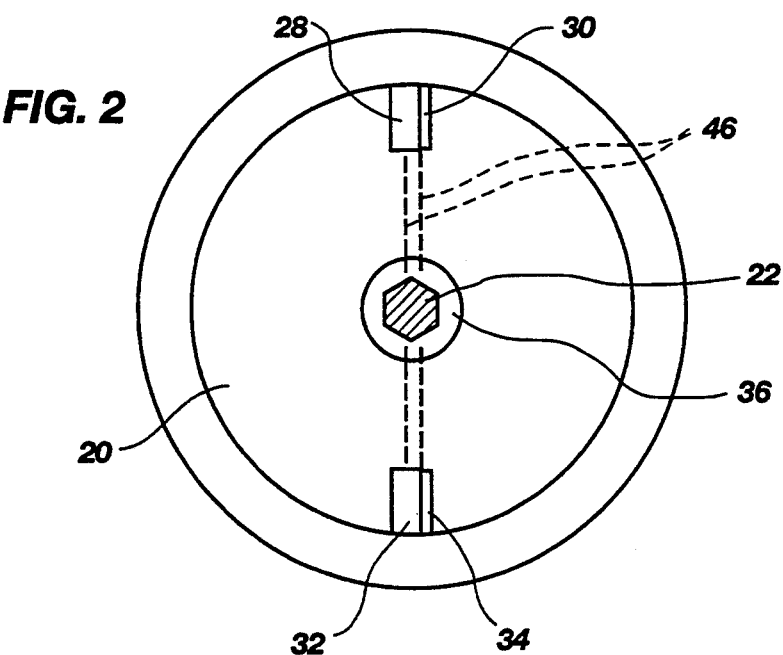

The sample embodiment in FIGS. 1 and 2 shows a rotor (20) through which a test object in the form of an elongated, prism-shaped section (22) with a hexagonal solid cross-section is fed in the direction of the arrows (24). The rotor (20) rotates around a longitudinal axis (26) of the section (22). A number of probes (28, 30, 32 and 34) are arranged in the rotor (20), with their central beams aimed at the section (22) to be tested. In a known fashion, the rotor (20) forms a probe-to-specimen contact chamber (36) which is filled with water in order to provide the sonic contact between the probes and the section (22). The probe-to-specimen contact chamber (36) is sealed at the sides with one left and one right sealing assembly (38); both of these sealing assemblies comprise elongated, tube-shaped arrangements in which the actual seals (40) are installed at the ends. Like the section (22) itself, the sealing assemblies (38) are not rotated. Their seals (40) have an opening corresponding to the shape of the section (22); the section (22) can be moved in relation to the seal assembly (38) in the direction of the arrow (24), thus providing for the sealing of the translational movement. The sealing of the rotational movement is provided between the outer shell of the sealing assemblies (38) and the corresponding inner shell of the rotor (20).

The probes (28, 30 and 32, 34) are arranged in each probe carrier (44), which in turn is a part of the rotor unit (20). The probes (28 to 34) can be displaced transversely within the probe carrier (44) in the plane represented in FIG. 2, which shows a transverse displacement of the probe pairs in each probe carrier (44). As a result, the central beams (46) of the two probes in each probe pair are laterally staggered and parallel to one another, as illustrated in FIG. 2. The full context of this arrangement is clearer in FIGS. 3 and 4, which are discussed below.

Figure 3:
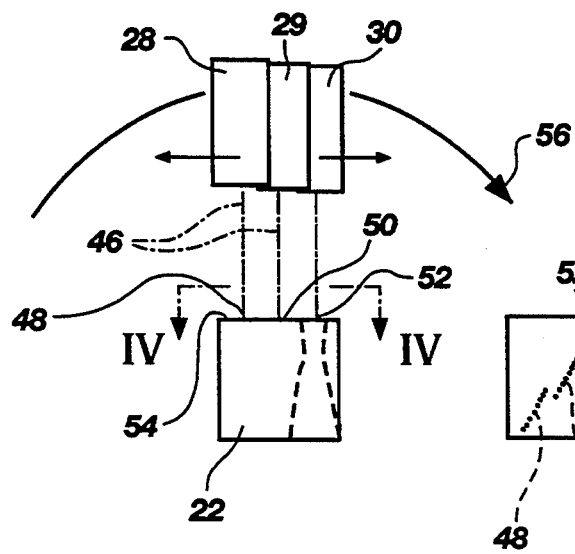

FIG. 3 shows three probes (28, 29, 30) arranged in a row along the longitudinal axis (26) of the section (22). These probes are displaced laterally in a single plane in relation to one another; this plane is a radial plane of the rotor (24), i.e. it is at right angles to the longitudinal section axis (26). The individual probes (28, 29, 30) are parallel to one another, and as a result their central beams (46) are also parallel, separated by the distance of the displacement of the probes. The beams contact a planar outer surface (54) of the section (22) at points of incidence (48, 50, 52). As a result of the rotation of the rotor (20), indicated by the arrow (56), the angle of the central beams (46) in relation to the planar outer surface (54) changes constantly. FIG. 3 shows a monetary condition at the point at which the central beams (46) are perpendicular to the planar outer surface (54). The dotted lines in FIG. 3 show the outline of the test zone within the cross-sectional area of the section (22) to be tested, corresponding to the shot fired from probe 30.

Figure 4:
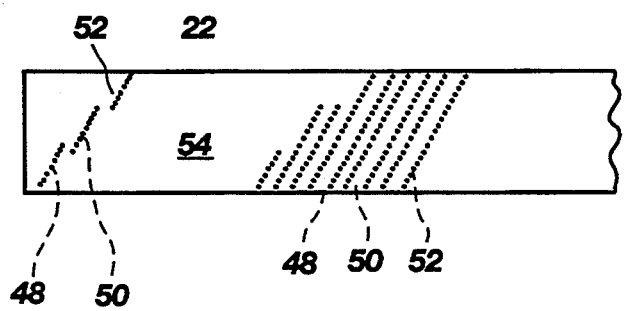

The probes (28, 29, 30) are triggered and emit ultrasonic impulses when the angle of their central beam in relation to the planar outer surface (54) is within a specific range, e.g. 90°+/−5°. The ultrasonic field emitted from the probes (28 to 30) has a certain amount of spread; this provides an echo for the specular reflection of the central beam from the planar outer surface (54) when the probes (28 to 30) are 5° before the position shown in FIG. 3 in the direction opposite to that indicated by the arrow (56). In order to make registration of this echo possible, at least one of the probes (28 to 30) emits a signal constantly and is also constantly on reception for a specular reflection signal. The valuation of the defect registration echo is disabled, however. As soon as described position 5° before the position shown in FIG. 3 is reached, determined by the increase in the specular reflection signal level, the evaluation circuitry is activated and the section is tested for defects (or its geometry is verified) within the next 10° of rotation of the rotor (20). The sequence of points resulting from the series of shots fired periodically from the probes (28 to 30) describes invisible points of incidence on the planar outer surface (54) in the form of dashes running at a parallel offset for the three probes (28 to 30). The left-hand section of FIG. 4 shows the points of incidence (48 to 52) obtained during a single rotation, i.e. for one appearance of the planar outer surface (54). This surface appears again with each rotation, however, and the combination of the linear feed of the section (22) and the rotation of the rotor (20) results in a pattern of points of incidence as indicated in the right-hand section of FIG. 4. The result is a complete volume test of the section; each point of incidence corresponds to a test zone as indicated by the dotted outline in FIG. 3. The lateral displacement of the probes (28 and 30) ensures that the edge zones of the section (22), which has a square cross-section in this example, are also scanned. The setup is arranged so that the section (22) is advanced by a distance corresponding to the offset between two probes (28, 29) or (29, 30) upon each rotation of the rotor (20). This results in an overlapping of the scanning tacks, as can be seen on the right-hand section in FIG. 4.

Figure 5:
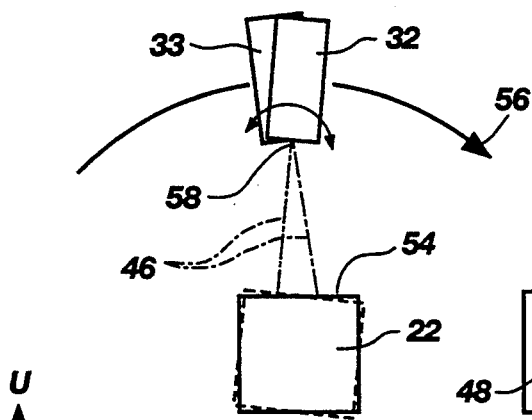
Figure 6:
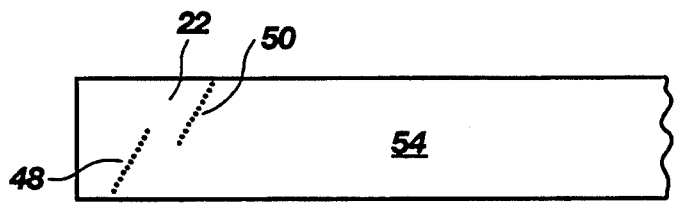

The sample embodiment in FIGS. 5 and 6 shows two probes (32, 33) which can be swivelled around an axis (58), independently of one another. In the embodiment shown in FIG. 5 the two probes (32, 33) are adjusted so that they are offset by an angle of +7° and −7° degrees, respectively, from a radial axis. The results of this arrangement is that the points of incidence (48, 50) are not in the centre of the planar outer surface (54) but rather to the left and right of it or above and below it, as shown in FIG. 6. The corresponding short, dash-shaped scanning tracks, composed of a large number of individual points of incidence, are indicated in FIG. 6; they correspond to the tracks shown in FIG. 4, with the difference that only two probes are used.

In the monetary image captured in FIG. 5, the two central beams (46) of the two probes (32, 33) are not perpendicular to the planar outer surface (54). However, upon further rotation in the sense indicated by the arrow (56), the central beam (46) of the rear probe (33) will become perpendicular to the planar outer surface (54). This condition is indicated for the front probe (32) with a section (22) shown rotated through the necessary angle of 7° (dotted outline). This representation makes it clear that the point of incidence wanders along the planar outer surface (54) in the course of the rotation of the rotor (20), as shown by the patterns of points in FIGS. 4 and 6.

The decisive difference in contrast to tube testing systems according to the current state of the art is thus that the testing electronics is only switched on when the angle between the probes and the planar outer surface (54) lies within a predetermined range. in the sample embodiments described here the probes, or at least one of the probes, are activated and emit ultrasonic impulses continuously. However, these impulses are only evaluated for specular reflections; when a signal for specular reflection is registered, the testing electronics are activated and a test is performed.

Figure 7:
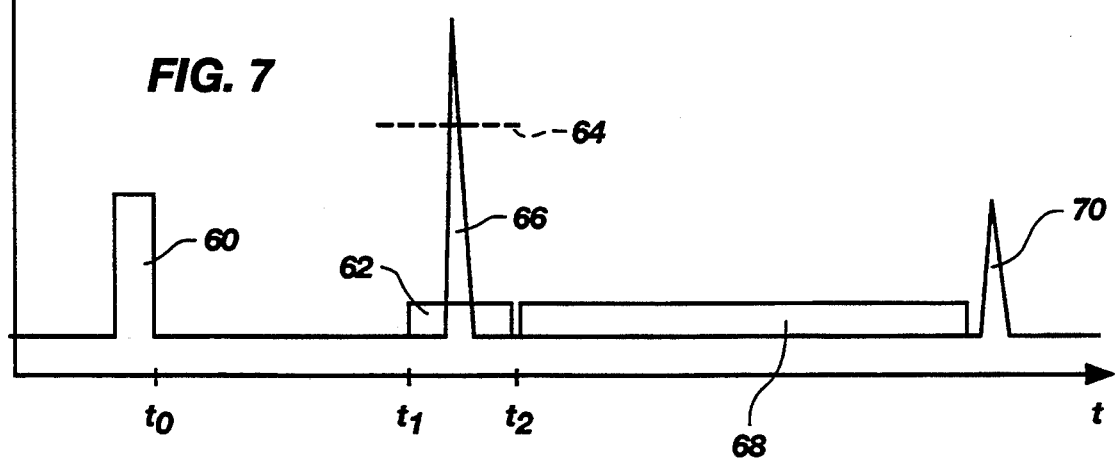

FIG. 7 shows the electrical sequence of events for the firing of a complete shot, with the development of the voltage U over a period of time t. A transmit impulse (60) is triggered at time t0. An aperture (62) is located between times t1 and t2 to allow the registration of the incidence of a specular reflection. If a signal higher than the threshold value (64) is registered within this aperture (62), such as signal (66) for example, the angle of the probe in question is within the predetermined range and within the divergence range allowed for specular reflection. In the course of the specular reflection condition the signal (66) first increases until it passes threshold value (64); it then continues to rise until the central beam is at an angle of 90° to the planar outer surface (54), then it falls, eventually dropping below the threshold value (64) again. A test is performed as long as the signal (66) lies above the threshold value (64). During this time, signals lying within a defect aperture (68) are processed. When signal (66) is below the threshold value (64), the processing of signals appearing within the defect aperture (68) is disabled. Signal (70) is a back wall echo typical for the type of setup shown in FIGS. 3 and 5. FIG. 7 makes it clear that a thin surface layer beneath the planar outer surface (54) and a corresponding surface layer in the area of the parallel back wall remain untested.

Instead of the registration of the relative angle between the sensors and the section (22) by means of specular reflection as described above, it is also possible to register the angle of rotation of the rotor (20) by means of appropriate arrangements, for example such as are described in DE-OS 25 57 062, already referred to above. The sensors (28 to 34) are then triggered when the angle between the central beams (46) and the planar outer surface (54) lies within the predetermined range.

Although the illustrated sample embodiments only show probes (28 to 34) with perpendicular beam emission, this should not be understood as a restriction. As alternatives to the probes shown it is also possible to use angled probes, arrays, wide-beam probes and other probe types. The process is suitable for any probe types, in particular SE, single probe and multiple probe operation.

The process according to the invention and devices operating according to this process allow testing of 100 percent of the volume of a section (22). All areas of the cross-sections of common sections can be scanned. The minimum size of registerable defects depends only how closely the points of incidence (48–52) are spaced on the planar outer surface (54).

It should be clear that in the case of a section (22) with a square cross-section, all four outer surfaces have the same status and a test as described above is performed on each outer surface. The same applies for sections with other cross-sections, e.g. hexagonal etc. The relative time during which a test is performed increases with the number of edges. In this sense, a round tube or bar can be regarded as a polygon with an infinite number of edges, for which the signal (66) is always above the threshold value (64), with the result that testing is performed continually. This means that the device for the implementation of the process can also be used for the testing of round material.

We claim:

1. Process for ultrasonic testing of elongated, prismatic workpieces, which workpieces have at least one planar outer surface extending along the longitudinal axis, to detect one of material defects and geometric data of the workpieces, wherein a workpiece to be tested is subjected to ultrasonic beams from several ultrasonic probes installed in a probe carrier, and the workpiece to be tested is fed along its longitudinal axis in relation to the probe carrier which is installed in a rotor of a rotary testing machine rotating about the longitudinal axis of the workpiece, the ultrasonic probes being installed in the probe carrier for displacement transversely to both the longitudinal axis and the direction of ultrasonic beams emitted by the ultrasonic probes, wherein the individual ultrasonic probes are adjusted so that central beams of said ultrasonic beams emitted by each ultrasonic probe impinge either simultaneously or at different times upon the planar outer surface of the workpiece at points of incidence which are adjacent to one another, thus forming adjacent scanning zones in the volume of the workpiece, and wherein the ultrasonic probes are activated individually by an arrangement for determining the angle of rotation between the rotor and the workpiece, the testing being only performed when the angle of rotation between a central beam of the ultrasonic beam emitted by an individual ultrasonic probe and the planar outer surface lies within a predetermined angular range of about 90°.

2. The process of claim 1, wherein the ultrasonic probes are installed in the probe carrier so that they can be displaced at right angles to on the one hand the longitudinal axis and on the other hand the direction of the ultrasonic beams emitted by the ultrasonic probes.

3. The process of claim 1, wherein said predetermined angular range is the range between 85° and 95°.

4. Process as claimed in claim 1, characterized by the fact that the determination of the angle between the rotor and the planar outer surface is performed by means of detecting a specular reflection of the central beam of at least one individual ultrasonic probe from the planar outer surface.

5. Process as claimed in claim 1, characterized by the fact that the angle of rotation of the rotor is registered; and by the fact that testing is only performed when, on the basis of the registered angle of rotation, the central beam of an individual ultrasonic probe and the planar outer surface lies within the predetermined angular range of about 90°.

6. Process as claimed in claim 1, characterized by the fact that at least one ultrasonic probe emits sound pulses continuously and periodically; and by the fact that the reflections of said pulses are received and evaluated by means of a time aperture for the signals originating from specularly reflected pulses and a threshold value; and by the fact that testing for defects or geometry is only performed while a signal above the threshold value is registered within the time aperture.

7. Process as claimed in claim 1, characterized by the fact that at least one probe is activated and emits ultrasonic pulses continuously and periodically; and by the fact that a time aperture for specular reflection signals is provided in a device for receiving reflected signals; and by the fact that the signals occurring within the time aperture are subject to a threshold switching arrangement; and by the fact that a defect aperture for defect signals is provided; and by the fact that defect evaluation is only performed when the signals occurring within the aperture lies above the threshold value.

8. Process for ultrasonic testing of elongated, prismatic, workpieces, which workpieces have at least one planar outer surface extending along the longitudinal axis, to detect one of material defects and geometric data of the workpieces, wherein a workpiece to be tested is subjected to ultrasonic beams from several ultrasonic probes installed in a probe carrier, and the workpiece to be tested is fed along its longitudinal axis in relation to the probe carrier which is installed in a rotor of a rotary testing machine rotating about the longitudinal axis of the workpiece, the ultrasonic probes being installed in the probe carrier so that the angular position thereof can be adjusted individually by swivelling about a swivel axis running parallel to the longitudinal axis, wherein the individual probes are adjusted so that central beams emitted by each probe impinge either simultaneously or at different times upon a planar outer surface of the workpiece at points of incidence which are adjacent to one another, thus forming adjacent scanning zones in the volume of the workpiece and wherein the ultrasonic probes are activated individually by an arrangement for determining the angle of rotation between the rotor and the workpiece, the testing being only performed when the angle of rotation between a central beam of the ultrasonic beam emitted by an individual ultrasonic probe and the planar outer surface lies within a predetermined angular range of about 90°.

9. Process of claim 8, wherein said predetermined angular range is the range between 85° and 95°.

* * * * *